United States Patent
Hirokami et al.

(10) Patent No.: US 9,169,275 B2
(45) Date of Patent: Oct. 27, 2015

(54) ORGANOPOLYSILOXANE AND MAKING METHOD

(71) Applicant: SHIN-ETSU CHEMICAL CO., LTD., Tokyo (JP)

(72) Inventors: Munenao Hirokami, Annaka (JP); Kazuhiro Tsuchida, Annaka (JP); Muneo Kudo, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 209 days.

(21) Appl. No.: 13/927,939

(22) Filed: Jun. 26, 2013

(65) Prior Publication Data
US 2014/0005431 A1    Jan. 2, 2014

(30) Foreign Application Priority Data
Jun. 27, 2012 (JP) ................................ 2012-143616

(51) Int. Cl.
*C07F 7/00* (2006.01)
*C07F 7/08* (2006.01)
*C08G 77/28* (2006.01)
*C08K 5/548* (2006.01)

(52) U.S. Cl.
CPC .............. *C07F 7/0834* (2013.01); *C08G 77/28* (2013.01); *C08K 5/548* (2013.01)

(58) Field of Classification Search
CPC .................................................... C07F 7/0834
USPC ............................................................ 556/427
See application file for complete search history.

(56) References Cited

U.S. PATENT DOCUMENTS

| 5,650,474 A | 7/1997 | Yamaya et al. |
| 5,814,703 A | 9/1998 | Yamaya et al. |
| 6,331,605 B1 | 12/2001 | Lunginsland et al. |
| 6,608,145 B1 * | 8/2003 | Lin et al. .................... 525/332.6 |
| 6,727,339 B2 | 4/2004 | Luginsland et al. |

FOREIGN PATENT DOCUMENTS

| EP | 0 964 021 B1 | 5/2004 |
| EP | 1 273 613 B1 | 7/2006 |
| JP | 7-292108 A | 11/1995 |
| JP | 9-111188 A | 4/1997 |
| JP | 4376999 B2 | 12/2009 |
| JP | 4615180 B2 | 1/2011 |

OTHER PUBLICATIONS

Extended European Search Report issued Apr. 10, 2014, in European Patent Application No. 13173492.3.

* cited by examiner

*Primary Examiner* — Porfirio Nazario Gonzalez
*Assistant Examiner* — Kofi Adzamli
(74) *Attorney, Agent, or Firm* — Birch, Stewart, Kolasch & Birch, LLP

(57) ABSTRACT

Organopolysiloxanes containing a sulfide-containing organic group, a long-chain alkyl group, and a hydrolyzable group are novel. The organopolysiloxanes are effective for improving the shelf stability of epoxy resin compositions.

7 Claims, No Drawings

ORGANOPOLYSILOXANE AND MAKING METHOD

CROSS-REFERENCE TO RELATED APPLICATION

This non-provisional application claims priority under 35 U.S.C. §119(a) on Patent Application No. 2012-143616 filed in Japan on Jun. 27, 2012, the entire contents of which are hereby incorporated by reference.

TECHNICAL FIELD

This invention relates to novel organopolysiloxanes containing a sulfide-containing organic group, long-chain alkyl group, and hydrolyzable group, and a method for preparing the same.

BACKGROUND ART

Organopolysiloxanes containing a mercapto group and a hydrolyzable group and their making methods are known in the art. For example, Patent Document 1 discloses a method of preparing an organopolysiloxane by hydrolytic condensation using a neutral fluorine compound as the catalyst. Patent Documents 2 and 3 disclose that organopolysiloxanes containing a mercapto and hydrolyzable group are used in coating compositions and rubber compositions. However, the compositions comprising an organopolysiloxane containing a mercapto and hydrolyzable group lack shelf stability because the mercapto group is active.

Also known are organopolysiloxanes containing a sulfide group and a hydrolyzable group and their making methods. For example, Patent Document 4 discloses an organopolysiloxane containing a sulfide and propyl group and a method of preparing the same.

However, organopolysiloxanes containing a sulfide-containing organic group, long-chain alkyl group, and hydrolyzable group are unknown.

CITATION LIST

Patent Document 1: JP-A H07-292108
Patent Document 2: JP-A H09-111188
Patent Document 3: JP 4615180 (EP 1273613, U.S. Pat. No. 6,727,339)
Patent Document 4: JP 4376999 (EP 0964021, U.S. Pat. No. 6,331,605)

DISCLOSURE OF INVENTION

An object of the invention is to provide a novel organopolysiloxane containing a sulfide-containing organic group, long-chain alkyl group, and hydrolyzable group, and a method for preparing the same.

The inventors have found that an organopolysiloxane containing a sulfide-containing organic group, long-chain alkyl group, and hydrolyzable group can be prepared by the method defined below. When this organopolysiloxane is added to epoxy and other resin compositions, the compositions are endowed with shelf stability.

In one aspect, the invention provides an organopolysiloxane containing at least a sulfide-containing organic group, a long-chain alkyl group, and a hydrolyzable group, represented by the average compositional formula (1):

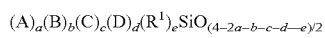  (1)

wherein A is a sulfide-containing divalent organic group, B is an alkyl group of 5 to 10 carbon atoms, C is a hydrolyzable group and/or hydroxyl group, D is a mercapto-containing organic group, $R^1$ is an alkyl group of 1 to 4 carbon atoms, or an aryl group of 6 to 10 carbon atoms, a, b, c, d and e are numbers in the range: $0<2a<1$, $0<b<1$, $0<c<3$, $0\le d<1$, $0\le e<2$, and $0<2a+b+c+d+e<4$.

Preferably, the sulfide-containing divalent organic group has the formula (2):

  (2)

wherein n is an integer of 1 to 10, x has a statistic average value of 1 to 6, *— and —* each denote a valence bond; the mercapto-containing organic group has the formula (3):

  (3)

wherein m is an integer of 1 to 10, and *— denotes a valence bond; the hydrolyzable group has the formula (4):

  (4)

wherein $R^2$ is an alkyl group of 1 to 20 carbon atoms, aryl group of 6 to 10 carbon atoms, aralkyl group of 7 to 10 carbon atoms, or alkenyl group of 2 to 10 carbon atoms, and *— denotes a valence bond.

Also preferably, d in formula (1) is $0<d<1$.

The organopolysiloxane defined herein can be prepared by subjecting the following reactants to cohydrolytic condensation, an organosilicon compound having the formula (5):

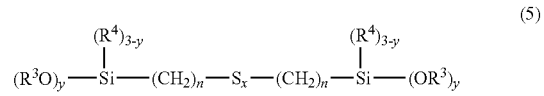  (5)

wherein n is an integer of 1 to 10, x has a statistic average value of 1 to 6, $R^3$ is an alkyl group of 1 to 20 carbon atoms, aryl group of 6 to 10 carbon atoms, aralkyl group of 7 to 10 carbon atoms, or alkenyl group of 2 to 10 carbon atoms, $R^4$ is an alkyl group of 1 to 10 carbon atoms or aryl group of 6 to 10 carbon atoms, and y is an integer of 1 to 3, an organosilicon compound having the formula (6):

  (6)

wherein $R^3$, $R^4$, and y are as defined above, and p is an integer of 5 to 10, an optional organosilicon compound having the formula (7):

  (7)

wherein $R^3$, $R^4$, m, and y are as defined above, and an optional organosilicon compound having the formula (8):

wherein $R^3$, $R^4$, and y are as defined above, and q is an integer of 1 to 4.

ADVANTAGEOUS EFFECTS OF INVENTION

The organopolysiloxane contains a sulfide-containing organic group and a long-chain alkyl group. Since an active mercapto group is sterically protected, a composition having the organopolysiloxane added thereto is significantly improved in shelf stability. The sulfide group may be cleaved in a chemically reductive manner with an acid or the like to form a mercapto group, which may be, in turn, cleaved with heat or the like to create a thiyl radical corresponding to the mercapto. Then this organopolysiloxane can be used as equivalent to the mercapto-functional organopolysiloxane.

DESCRIPTION OF PREFERRED EMBODIMENTS

One embodiment of the invention is an organopolysiloxane containing a sulfide-containing organic group, a long-chain alkyl group, and a hydrolyzable group. It is represented by the average compositional formula (1):

$$(A)_a(B)_b(C)_c(D)_d(R^1)_e SiO_{(4-2a-b-c-d-e)/2} \quad (1)$$

wherein A is a sulfide-containing divalent organic group, B is an alkyl group of 5 to 10 carbon atoms, C is a hydrolyzable group and/or hydroxyl group, D is a mercapto-containing organic group, R' is an alkyl group of 1 to 4 carbon atoms, or an aryl group of 6 to 10 carbon atoms, a, b, c, d and e are numbers in the range: $0<2a<1$, $0<b<1$, $0<c<3$, $0\leq d<1$, $0\leq e<2$, and $0<2a+b+c+d+e<4$.

Each of a, b, d and e denotes an average molar amount of the relevant organic group provided that the total molar amount of silicon atoms is unity (1), and indicates the average molar percent in which the relevant organic group is present per molecule. It is thus understood that $2a+b+d+e=1$. The term "2a" is given because A is a divalent organic group. Further, c indicates the average molar percent in which the hydrolyzable group on silicon is present per mole of silicon atoms.

Specifically, the sulfide-containing divalent organic group of A has the formula (2):

$$*-(CH_2)_n-S_x-(CH_2)_n-* \quad (2)$$

wherein n is an integer of 1 to 10, preferably 2 to 4, x has a statistic average value of 1 to 6, preferably 2 to 4. The mercapto-containing organic group of D has the formula (3):

$$*-(CH_2)_m-SH \quad (3)$$

wherein m is an integer of 1 to 10, preferably 1 to 5. The hydrolyzable group of C has the formula (4):

$$*-OR^2 \quad (4)$$

wherein $R^2$ is an alkyl group of 1 to 20 carbon atoms, preferably 1 to 5 carbon atoms, and more preferably 1 to 3 carbon atoms, an aryl group of 6 to 10 carbon atoms, an aralkyl group of 7 to 10 carbon atoms, or an alkenyl group of 2 to 10 carbon atoms, preferably 2 to 4 carbon atoms. In these formulae, *— and —* each denote a valence bond.

Preferred examples of the monovalent hydrocarbon group of 5 to 10 carbon atoms represented by B include straight, branched or cyclic alkyl groups such as pentyl, hexyl, octyl and decyl. Examples of the monovalent hydrocarbon group of 1 to 4 carbon atoms represented by $R^1$ include methyl, ethyl, and propyl.

Examples of the sulfide-containing divalent organic group include —$CH_2S_2$—$CH_2$—, —$C_2H_4$—$S_2$—$C_2H_4$—, —$C_3H_6$—$S_2$—$C_3H_6$—, —$C_4H_8$—$S_2$—$C_4H_8$—, —$CH_2$—$S_4$—$CH_2$—, —$C_3H_6$—$S_4$—$C_3H_6$—, and —$C_4H_8$—$S_4$—$C_4H_8$—.

Examples of the mercapto-containing organic group include —$CH_2SH$, —$C_2H_4SH$, —$C_3H_6SH$, —$C_4H_8SH$, —$C_5H_{10}SH$, —$C_6H_{12}SH$, —$C_7H_{14}SH$, —$C_8H_{16}SH$, —$C_9H_{18}SH$, and —$C_{10}H_{20}SH$.

Of the groups of $R^2$, suitable alkyl groups include methyl, ethyl, propyl, butyl, hexyl, octyl, decyl and octadecyl. Suitable aryl groups include phenyl and tolyl. A typical aralkyl group is benzyl. Suitable alkenyl groups include vinyl, propenyl and pentenyl.

Preferred are those organopolysiloxanes containing a sulfide-containing organic group, a long-chain alkyl group, a mercapto-containing organic group, and a hydrolyzable group in a molecule, represented by the average compositional formula (1) wherein d is $0<d<1$. More preferably, the ranges of a, b, c, d and e are $0.05 \leq 2a \leq 0.9$, $0.05 \leq b \leq 0.9$, $0 \leq c \leq 2.0$, $0.05 \leq d \leq 0.8$, $0 \leq e \leq 0.1$, and $1 < 2a+b+c+d+e \leq 3$, especially $2 \leq 2a+b+c+d+e \leq 3$, and even more preferably $0.1 \leq 2a \leq 0.5$, $0.2 \leq b \leq 0.8$, $1.0 \leq c \leq 1.7$, $0.1 \leq d \leq 0.4$, and $0 \leq e \leq 0.05$.

The organopolysiloxane of the invention should preferably have a weight average molecular weight (Mw) of 400 to 10,000, more preferably 500 to 5,000, and even more preferably 600 to 2,000, as measured by gel permeation chromatography (GPC) versus polystyrene standards. Too low values of Mw suggest that noticeable portions of organosilicon reactants may be left unreacted whereas an organopolysiloxane having too high a Mw may be highly viscous or even solidify, indicating difficulty of handling.

In another embodiment, the organopolysiloxane is prepared by subjecting the following reactants to cohydrolytic condensation, an organosilicon compound having the formula (5):

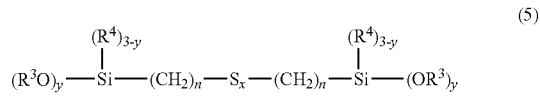

wherein n and x are as defined above, $R^3$ is an alkyl group of 1 to 20 carbon atoms, preferably 1 to 5 carbon atoms, an aryl group of 6 to 10 carbon atoms, an aralkyl group of 7 to 10 carbon atoms, or an alkenyl group of 2 to 10 carbon atoms, preferably 2 to 4 carbon atoms, $R^4$ is an alkyl group of 1 to 10 carbon atoms, preferably 1 to 3 carbon atoms, or an aryl group of 6 to 10 carbon atoms, and y is an integer of 1 to 3, preferably 2 or 3, an organosilicon compound having the formula (6):

wherein $R^3$, $R^4$, and y are as defined above, and p is an integer of 5 to 10, optionally, an organosilicon compound having the formula (7):

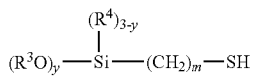
(7)

wherein $R^3$, $R^4$, m, and y are as defined above, and optionally, an organosilicon compound having the formula (8):

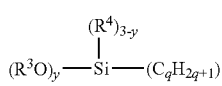
(8)

wherein $R^3$, $R^4$, and y are as defined above, and q is an integer of 1 to 4, preferably 1 to 3.

Of the groups of $R^3$, suitable alkyl groups include methyl, ethyl, propyl, butyl, hexyl, octyl, decyl and octadecyl; suitable aryl groups include phenyl, tolyl and naphthyl; suitable alkenyl groups include vinyl, propenyl and pentenyl. Of the groups of $R^4$, suitable alkyl groups include methyl, ethyl, propyl, butyl, hexyl, octyl, decyl and octadecyl; suitable aryl groups include phenyl, tolyl and naphthyl; suitable aralkyl groups include benzyl and ethylphenyl.

Examples of the organosilicon compound having formula (5) include, but are not limited to, bis(trimethoxysilylpropyl)tetrasulfide, bis(triethoxysilylpropyl)tetrasulfide, bis(trimethoxysilylpropyl)disulfide, and bis(triethoxysilylpropyl)disulfide.

Examples of the organosilicon compound having formula (6) include, but are not limited to, pentyltrimethoxysilane, pentylmethyldimethoxysilane, pentyltriethoxysilane, pentylmethyldiethoxysilane, hexyltrimethoxysilane, hexylmethyldimethoxysilane, hexyltriethoxysilane, hexylmethyldiethoxysilane, octyltrimethoxysilane, octylmethyldimethoxysilane, octyltriethoxysilane, octylmethyldiethoxysilane, decyltrimethoxysilane, decylmethyldimethoxysilane, decyltriethoxysilane, and decylmethyldiethoxysilane.

Examples of the organosilicon compound having formula (7) include, but are not limited to, α-mercaptomethyltrimethoxysilane, α-mercaptomethylmethyldimethoxysilane, α-mercaptomethyltriethoxysilane, α-mercaptomethylmethyldiethoxysilane, α-mercaptopropyltrimethoxysilane, α-mercaptopropylmethyldimethoxysilane, α-mercaptopropyltriethoxysilane, and α-mercaptopropylmethyldiethoxysilane.

Examples of the organosilicon compound having formula (8) include, but are not limited to, methyltrimethoxysilane, dimethyldimethoxysilane, methyltriethoxysilane, methylethyldiethoxysilane, propyltrimethoxysilane, propylmethyldimethoxysilane, and propylmethyldiethoxysilane.

The amounts of the organosilicon compounds having formulae (5) to (8) used are selected such that a to e in formula (1) may fall in the range disclosed herein. Specifically, an appropriate amount of the organosilicon compound having formula (5) is 5 to 90 mol %, more preferably 10 to 50 mol %, an appropriate amount of the organosilicon compound having formula (6) is 10 to 95 mol %, more preferably 20 to 80 mol %, an appropriate amount of the organosilicon compound having formula (7) is 0 to 85 mol %, more preferably 10 to 40 mol %, and an appropriate amount of the organosilicon compound having formula (8) is 0 to 10 mol %, more preferably 0 to 5 mol %, based on the total of the organosilicon compounds having formulae (5) to (8).

Cohydrolytic condensation may be performed by any well-known techniques. Water may be used in a standard amount, typically 0.5 to 0.99 mole, preferably 0.66 to 0.90 mole per mole of all hydrolyzable silyl groups.

In the method for the preparation of organopolysiloxane, the reaction may be carried out in an organic solvent, if desired. Although the solvent used herein is not particularly limited, suitable solvents include aliphatic hydrocarbon solvents such as pentane, hexane, heptane, and decane; ether solvents such as diethyl ether, tetrahydrofuran and 1,4-dioxane; amide solvents such as formamide, dimethylformamide and N-methylpyrrolidone; aromatic hydrocarbon solvents such as benzene, toluene and xylene; and alcohol solvents such as methanol, ethanol and propanol. Inter alia, ethanol and isopropanol are preferred for effective hydrolytic reaction. When used, the amount of the solvent is not particularly limited. An appropriate amount of the solvent is up to twice the weight of organosilicon compounds, preferably up to equivalent.

Also in the method for the preparation of organopolysiloxane, a catalyst may be used, if desired. Although the catalyst used herein is not particularly limited, suitable catalysts include acidic catalysts such as hydrochloric acid and acetic acid; Lewis acid catalysts such as tetrabutylorthotitanate and ammonium fluoride; alkali metal salts such as sodium hydroxide, potassium hydroxide, sodium carbonate, sodium acetate, potassium acetate, sodium hydrogencarbonate, potassium carbonate, potassium hydrogencarbonate, calcium carbonate, sodium methoxide, and sodium ethoxide; and amine compounds such as triethylamine, tributylamine, pyridine, and 4-dimethylaminopyridine. For instance, hydrochloric acid may be used as the catalyst for hydrolytic reaction (and/or partial condensation) of silanes and potassium hydroxide be used as the catalyst for condensation or oligomerization of silanols. An appropriate amount of the catalyst used is 0.001 to 0.05 mole equivalent per mole of all hydrolyzable silyl groups. Notably, this amount is an amount of each catalyst when the catalyst for hydrolytic reaction of silanes and the catalyst for condensation reaction of silanols are used in combination.

Typically cohydrolytic condensation reaction may be performed at a temperature of 20 to 100° C., preferably 60 to 85° C.

The organopolysiloxanes of the invention are useful as resin modifier or the like.

EXAMPLE

Examples and Comparative Examples are given below by way of illustration and not by way of limitation. A weight average molecular weight (Mw) is measured by gel permeation chromatography (GPC) versus polystyrene standards. All reactants named KBE (e.g., KBE-846) are commercially available from Shin-Etsu Chemical Co., Ltd.

Example 1

A 2-L separable flask equipped with a stirrer, reflux condenser, dropping funnel and thermometer was charged with 215.6 g (0.4 mol) of bis(triethoxysilylpropyl)tetrasulfide (KBE-846), 442.4 g (1.6 mol) of octyltriethoxysilane (KBE-3083), and 162.0 g of ethanol. A mixture of 32.4 g of 0.5N aqueous hydrochloric acid (1.8 mol of water) and 75.6 g of ethanol was added dropwise to the flask at room temperature, followed by stirring at 80° C. for 2 hours. The reaction solution was filtered, and 15.7 g of 5 wt % KOH/EtOH solution was added dropwise to the filtrate, which was stirred at 80° C. for 2 hours. This was followed by concentration under reduced pressure and filtration, yielding 494.1 g of a brown clear liquid. On analysis, the resulting silicone oligomer had a Mw of 880 as measured by GPC and was identified to have the following average compositional formula.

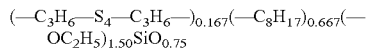

This is designated Oligomer #1.

Example 2

A 2-L separable flask equipped with a stirrer, reflux condenser, dropping funnel and thermometer was charged with 215.6 g (0.4 mol) of bis(triethoxysilylpropyl)tetrasulfide (KBE-846) and 50.0 g of ethanol. With stirring, a mixture of 7.2 g of 0.5N aqueous HCl (0.40 mol of water) and 16.8 g of ethanol was added dropwise to the flask at room temperature, followed by stirring at room temperature for 30 minutes. Another 1-L separable flask equipped with a stirrer, reflux condenser, dropping funnel and thermometer was charged with 442.4 g (1.6 mol) of octyltriethoxysilane (KBE-3083) and 112.0 g of ethanol. With stirring, a mixture of 14.4 g of 0.5N aqueous HCl (0.80 mol of water) and 33.6 g of ethanol was added dropwise to the flask at room temperature, followed by stirring at room temperature for 30 minutes. This reaction solution was added dropwise to the former 2-L flask. Then a mixture of 10.8 g of 0.5N aqueous HCl (0.60 mol of water) and 25.2 g of ethanol was added dropwise to the flask, followed by stirring at 80° C. for 2 hours. Further 15.7 g of 5 wt % KOH/EtOH solution was added dropwise, followed by stirring at 80° C. for 2 hours. This was followed by vacuum distillation and filtration, yielding 489.3 g of a brown clear liquid. On analysis, the resulting silicone oligomer had a Mw of 870 as measured by GPC and was identified to have the following average compositional formula.

$(-C_3H_6-S_4-C_3H_6-)_{0.167}(-C_8H_{17})_{0.667}(-OC_2H_5O)_{1.50}SiO_{0.75}$

This is designated Oligomer #2.

Example 3

A 2-L separable flask equipped with a stirrer, reflux condenser, dropping funnel and thermometer was charged with 107.8 g (0.2 mol) of bis(triethoxysilylpropyl)tetrasulfide (KBE-846), 95.4 g (0.4 mol) of γ-mercaptopropyltriethoxysilane (KBE-803), 442.4 g (1.6 mol) of octyltriethoxysilane (KBE-3083), and 162.0 g of ethanol. A mixture of 32.4 g of 0.5N aqueous hydrochloric acid (1.8 mol of water) and 75.6 g of ethanol was added dropwise to the flask at room temperature, followed by stirring at 80° C. for 2 hours. The reaction solution was filtered, and 14.6 g of 5 wt % KOH/EtOH solution was added dropwise to the filtrate, which was stirred at 80° C. for 2 hours. This was followed by concentration under reduced pressure and filtration, yielding 490.1 g of a brown clear liquid. On analysis, the resulting silicone oligomer had a Mw of 860 as measured by GPC and was identified to have the following average compositional formula.

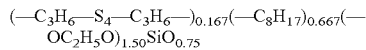

This is designated Oligomer #3.

Example 4

A 2-L separable flask equipped with a stirrer, reflux condenser, dropping funnel and thermometer was charged with 107.8 g (0.2 mol) of bis(triethoxysilylpropyl)tetrasulfide (KBE-846), 95.4 g (0.4 mol) of γ-mercaptopropyltriethoxysilane (KBE-803), and 50.0 g of ethanol. With stirring, a mixture of 7.2 g of 0.5N aqueous HCl (0.40 mol of water) and 16.8 g of ethanol was added dropwise to the flask at room temperature, followed by stirring at room temperature for 30 minutes. Another 1-L separable flask equipped with a stirrer, reflux condenser, dropping funnel and thermometer was charged with 442.4 g (1.6 mol) of octyltriethoxysilane (KBE-3083) and 112.0 g of ethanol. With stirring, a mixture of 14.4 g of 0.5N aqueous HCl (0.80 mol of water) and 33.6 g of ethanol was added dropwise to the flask at room temperature, followed by stirring at room temperature for 30 minutes. This reaction solution was added dropwise to the former 2-L flask. Then a mixture of 10.8 g of 0.5N aqueous HCl (0.60 mol of water) and 25.2 g of ethanol was added dropwise to the flask, followed by stirring at 80° C. for 2 hours. Further 14.6 g of 5 wt % KOH/EtOH solution was added dropwise, followed by stirring at 80° C. for 2 hours. This was followed by vacuum distillation and filtration, yielding 488.1 g of a brown clear liquid. On analysis, the resulting silicone oligomer had a Mw of 860 as measured by GPC and was identified to have the following average compositional formula.

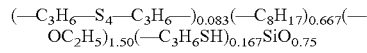

This is designated Oligomer #4.

Example 5

A 2-L separable flask equipped with a stirrer, reflux condenser, dropping funnel and thermometer was charged with 107.8 g (0.2 mol) of bis(triethoxysilylpropyl)tetrasulfide (KBE-846), 95.4 g (0.4 mol) of γ-mercaptopropyltriethoxysilane (KBE-803), 428.6 g (1.55 mol) of octyltriethoxysilane (KBE-3083), 8.9 g (0.05 mol) of methyltriethoxysilane (KBE-13), and 162.0 g of ethanol. A mixture of 32.4 g of 0.5N aqueous hydrochloric acid (1.8 mol of water) and 75.6 g of ethanol was added dropwise to the flask at room temperature, followed by stirring at 80° C. for 2 hours. The reaction solution was filtered, and 14.6 g of 5 wt % KOH/EtOH solution was added dropwise to the filtrate, which was stirred at 80° C. for 2 hours. This was followed by concentration under reduced pressure and filtration, yielding 481.1 g of a brown clear liquid. On analysis, the resulting silicone oligomer had a Mw of 850 as measured by GPC and was identified to have the following average compositional formula.

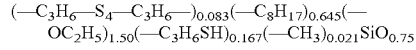

This is designated Oligomer #5.

Example 6

A 2-L separable flask equipped with a stirrer, reflux condenser, dropping funnel and thermometer was charged with 107.8 g (0.2 mol) of bis(triethoxysilylpropyl)tetrasulfide (KBE-846), 95.4 g (0.4 mol) of γ-mercaptopropyltriethoxysilane (KBE-803), and 50.0 g of ethanol. With stirring, a mixture of 7.2 g of 0.5N aqueous HCl (0.40 mol of water) and 16.8 g of ethanol was added dropwise to the flask at room temperature, followed by stirring at room temperature for 30 minutes. Another 1-L separable flask equipped with a stirrer, reflux condenser, dropping funnel and thermometer was charged with 428.6 g (1.55 mol) of octyltriethoxysilane (KBE-3083), 8.9 g (0.05 mol) of methyltriethoxysilane (KBE-13), and 112.0 g of ethanol. With stirring, a mixture of 14.4 g of 0.5N aqueous HCl (0.80 mol of water) and 33.6 g of ethanol was added dropwise to the flask at room temperature, followed by stirring at room temperature for 30 minutes. This reaction solution was added dropwise to the former 2-L flask. Then a mixture of 10.8 g of 0.5N aqueous HCl (0.60 mol of water) and 25.2 g of ethanol was added dropwise to the flask, followed by stirring at 80° C. for 2 hours. Further 14.6 g of 5 wt % KOH/EtOH solution was added dropwise, followed by stirring at 80° C. for 2 hours. This was followed by vacuum distillation and filtration, yielding 480.3 g of a brown clear liquid. On analysis, the resulting silicone oligomer had a Mw of 850 as measured by GPC and was identified to have the following average compositional formula.

$(-C_3H_6-S_4-C_3H_6-)_{0.083}(-C_8H_{17})_{0.645}(-OC_2H_5)_{1.50}(-C_3H_6SH)_{0.167}(-CH_3)_{0.021}SiO_{0.75}$

This is designated Oligomer #6.

Comparative Example 1

A 2-L separable flask equipped with a stirrer, reflux condenser, dropping funnel and thermometer was charged with 572.4 g (2.4 mol) of γ-mercaptopropyltriethoxysilane (KBE-803) and 162.0 g of ethanol. A mixture of 32.4 g of 0.5N aqueous hydrochloric acid (1.8 mol of water) and 75.6 g of ethanol was added dropwise to the flask at room temperature, followed by stirring at 80° C. for 2 hours. The reaction solution was filtered, and 15.7 g of 5 wt % KOH/EtOH solution was added dropwise to the filtrate, which was stirred at 80° C. for 2 hours. This was followed by concentration under reduced pressure and filtration, yielding 420.1 g of a colorless clear liquid. On analysis, the resulting silicone oligomer had a Mw of 750 as measured by GPC and was identified to have the following average compositional formula.

$-C_3H_6-SH)_{1.0}(-OC_2H_5)_{1.50}SiO_{0.75}$

This is designated Oligomer #7.

Comparative Example 2

A 2-L separable flask equipped with a stirrer, reflux condenser, dropping funnel and thermometer was charged with 107.8 g (0.2 mol) of bis(triethoxysilylpropyl)tetrasulfide (KBE-846), 95.4 g (0.4 mol) of γ-mercaptopropyltriethoxysilane (KBE-803), 330.2 g (1.6 mol) of propyltriethoxysilane (KBE-3033), and 162.0 g of ethanol. A mixture of 32.4 g of 0.5N aqueous hydrochloric acid (1.8 mol of water) and 75.6 g of ethanol was added dropwise to the flask at room temperature, followed by stirring at 80° C. for 2 hours. The reaction solution was filtered, and 14.6 g of 5 wt % KOH/EtOH solution was added dropwise to the filtrate, which was stirred at 80° C. for 2 hours. This was followed by concentration under reduced pressure and filtration, yielding 368.9 g of a brown clear liquid. On analysis, the resulting silicone oligomer had a Mw of 690 as measured by GPC and was identified to have the following average compositional formula.

$(-C_3H_6-S_4-C_3H_6-)_{0.083}(-C_3H_7)_{0.667}(-OC_2H_5)_{1.50}(-C_3H_6SH)_{0.167}SiO_{0.75}$

This is designated Oligomer #8.

Reference Examples 1 to 6 and Comparative Reference Examples 1 to 2

Resin compositions were prepared by blending each of Oligomers #1 to #8 (in Examples 1 to 6 and Comparative Examples 1 to 2) with a phenolic resin, epoxy resin and cure accelerator according to the recipe of Table 1. The phenolic resin is TD-2131 by DIC Corp., the epoxy resin is YD-128 by Toto Chemical Co., Ltd., and the cure accelerator is triphenylphosphine. As a shelf stability test, the resin composition was aged at room temperature. The composition was rated good (○) for no gelation after 1 month, mediocre (Δ) when gelled after 1 month, and poor (×) when gelled after 1 week.

A ceramic substrate of alumina was immersed in the resin composition, pulled up at a constant rate of 50 mm/min, and heated at 120° C. for 1 hour and at 150° C. for 2 hours for curing the coating. The adhesion of the coating was examined by a cross-hatch test according to JIS K-5400 and reported as the number of sound sections per 100 sections.

TABLE 1

| Composition (pbw) | Reference Example | | | | | | Comparative Reference Example | |
|---|---|---|---|---|---|---|---|---|
| | 1 | 2 | 3 | 4 | 5 | 6 | 1 | 2 |
| Phenolic resin | 45 | 45 | 45 | 45 | 45 | 45 | 45 | 45 |
| Epoxy resin | 50 | 50 | 50 | 50 | 50 | 50 | 50 | 50 |
| Cure accelerator | 0.5 | 0.5 | 0.5 | 0.5 | 0.5 | 0.5 | 0.5 | 0.5 |
| Oligomer #1 | 4.5 | | | | | | | |
| Oligomer #2 | | 4.5 | | | | | | |
| Oligomer #3 | | | 4.5 | | | | | |
| Oligomer #4 | | | | 4.5 | | | | |
| Oligomer #5 | | | | | 4.5 | | | |
| Oligomer #6 | | | | | | 4.5 | | |
| Oligomer #7 | | | | | | | 4.5 | |
| Oligomer #8 | | | | | | | | 4.5 |
| Adhesion | 100/100 | 100/100 | 100/100 | 100/100 | 100/100 | 100/100 | 100/100 | 100/100 |
| Shelf stability | ○ | ○ | ○ | ○ | ○ | ○ | X | Δ |

The test results demonstrate that the resin compositions corresponding to Examples remain shelf stable, and the inventive organopolysiloxanes are effective.

Japanese Patent Application No. 2012-143616 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An organopolysiloxane containing at least a sulfide-containing organic group, a long-chain alkyl group, and a hydrolyzable group, represented by the average compositional formula (1):

$$(A)_a(B)_b(C)_c(D)_d(R^1)_e SiO_{(4-2a-b-c-d-e)/2} \quad (1)$$

wherein A is a sulfide-containing divalent organic group, B is an alkyl group of 5 to 10 carbon atoms, C is a hydrolyzable group and/or hydroxyl group, D is a mercapto-containing organic group, $R^1$ is an alkyl group of 1 to 4 carbon atoms, or an aryl group of 6 to 10 carbon atoms, a, b, c, d and e are numbers in the range: $0<2a<1, 0<b<1, 0<c<3, 0\le d<1, 0\le e<2$, and $0<2a+b+c+d+e<4$.

2. The organopolysiloxane of claim 1 wherein the sulfide-containing divalent organic group has the formula (2):

$$*-(CH_2)_n-S_x-(CH_2)-* \quad (2)$$

wherein n is an integer of 1 to 10, x has a statistic average value of 1 to 6, *— and —* each denote a valence bond, the mercapto-containing organic group has the formula (3):

$$*-(CH_2)_m-SH \quad (3)$$

wherein m is an integer of 1 to 10, and *— denotes a valence bond, the hydrolyzable group has the formula (4):

$$*-OR^2 \quad (4)$$

wherein $R^2$ is an alkyl group of 1 to 20 carbon atoms, aryl group of 6 to 10 carbon atoms, aralkyl group of 7 to 10 carbon atoms, or alkenyl group of 2 to 10 carbon atoms, and *— denotes a valence bond.

3. The organopolysiloxane of claim 1 wherein in the average compositional formula (1), d is $0<d<1$.

4. The organopolysiloxane of claim 1 wherein the average compositional formula (1), $0.05\le 2a\le 0.9$, $0.05\le b\le 0.9$, $1.0\le c\le 2.0$, $0.05\le d\le 0.8$, $0\le e\le 1$, and $2\le 2a+b+c+d+e\le 3$.

5. A method for preparing the organopolysiloxane of claim 1, comprising subjecting the following reactants to cohydrolytic condensation,
an organosilicon compound having the formula (5):

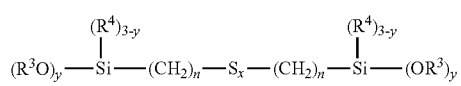

wherein n is an integer of 1 to 10, x has a statistic average value of 1 to 6, $R^3$ is an alkyl group of 1 to 20 carbon atoms, aryl group of 6 to 10 carbon atoms, aralkyl group of 7 to 10 carbon atoms, or alkenyl group of 2 to 10 carbon atoms, $R^4$ is an alkyl group of 1 to 10 carbon atoms or aryl group of 6 to 10 carbon atoms, and y is an integer of 1 to 3,
an organosilicon compound having the formula (6):

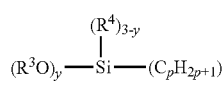

wherein $R^3$, $R^4$, and y are as defined above, and p is an integer of 5 to 10,
an optional organosilicon compound having the formula (7):

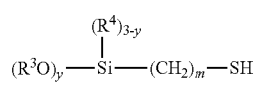

wherein $R^3$, $R^4$, m, and y are as defined above, and an optional organosilicon compound having the formula (8):

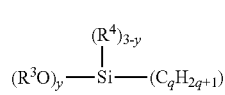

wherein $R^3$, $R^4$, and y are as defined above, and q is an integer of 1 to 4.

6. The method of claim 5 wherein an amount of the organosilicon compound having formula (5) is 10 to 50 mol %, an amount of the organosilicon compound having formula (6) is 20 to 80 mol %, an amount of the organosilicon compound having formula (7) is 10 to 40 mol %, and an amount of the organosilicon compound having formula (8) is 0 to 5 mol %.

7. The organopolysiloxane of claim 1 which a hydrolytic condensate of an organosilicon compound having the formula (5):

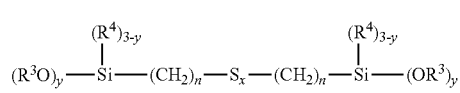

wherein n is an integer of 1 to 10, x has a statistic average value of 1 to 6, $R^3$ is an alkyl group of 1 to 20 carbon atoms, aryl group of 6 to 10 carbon atoms, aralkyl group of 7 to 10 carbon atoms, or alkenyl group of 2 to 10 carbon atoms, $R^4$ is an alkyl group of 1 to 10 carbon atoms or aryl group of 6 to 10 carbon atoms, and y is an integer of 1 to 3,
an organosilicon compound having the formula (6):

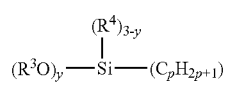

wherein $R^3$, $R^4$, and y are as defined above, and p is an integer of 5 to 10,
an optional organosilicon compound having the formula (7):

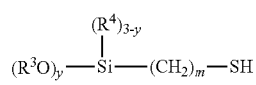

wherein $R^3$, $R^4$, m, and y are as defined above, and an optional organosilicon compound having the formula (8):

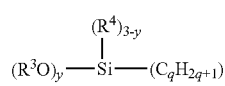

wherein $R^3$, $R^4$, and y are as defined above, and q is an integer of 1 to 4.

* * * * *